US012753280B2

(12) United States Patent
Park et al.

(10) Patent No.: US 12,753,280 B2
(45) Date of Patent: Oct. 6, 2026

(54) PURIFICATION METHOD FOR LAUROLACTAM

(71) Applicant: HANWHA SOLUTIONS CORPORATION, Seoul (KR)

(72) Inventors: Jeongseok Park, Daejeon (KR); Jinho Park, Daejeon (KR); Namjin Jang, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 593 days.

(21) Appl. No.: 18/262,214

(22) PCT Filed: Jan. 20, 2022

(86) PCT No.: PCT/KR2022/001030
§ 371 (c)(1),
(2) Date: Aug. 8, 2023

(87) PCT Pub. No.: WO2022/158872
PCT Pub. Date: Jul. 28, 2022

(65) Prior Publication Data
US 2024/0076450 A1 Mar. 7, 2024

(30) Foreign Application Priority Data
Jan. 20, 2021 (KR) ........................ 10-2021-0007868

(51) Int. Cl.
*C08G 69/18* (2006.01)
*C07D 201/16* (2006.01)
*C07D 225/02* (2006.01)

(52) U.S. Cl.
CPC ........... *C08G 69/18* (2013.01); *C07D 201/16* (2013.01); *C07D 225/02* (2013.01)

(58) Field of Classification Search
CPC ..... C08G 69/18; C07D 201/16; C07D 225/02
USPC .......................................................... 528/367
See application file for complete search history.

(56) References Cited

U.S. PATENT DOCUMENTS 3,196,178 A * 7/1965 Moody ................. C07C 233/09 203/91
8,399,658 B2 3/2013 Hengstermann

FOREIGN PATENT DOCUMENTS

| | | | |
|---|---|---|---|
| JP | 1974013191 | A | 2/1974 |
| JP | 2002003470 | A | 1/2002 |
| JP | 2004059553 | A | 2/2004 |
| JP | 2019104915 | A | 6/2019 |
| JP | 2023504265 | A | 2/2023 |
| JP | 2023550492 | A | 12/2023 |
| KR | 20190052621 | A | 5/2019 |
| KR | 20190080535 | A | 7/2019 |
| KR | 20200076288 | A | 6/2020 |
| WO | 2008012480 | A2 | 1/2008 |
| WO | 2008096873 | A1 | 8/2008 |
| WO | 2013099423 | A1 | 7/2013 |
| WO | 2019098569 | A1 | 5/2019 |
| WO | 2019098570 | A1 | 5/2019 |

OTHER PUBLICATIONS

Fujita et al., JP 2004-059553 A machine translation in English, Feb. 26, 2004. (Year: 2004).*
The JP Office action issued on Sep. 3, 2024.
An office action issued on Oct. 14, 2023, for corresponding KR Patent Application.
European Search Report issued on Apr. 4, 2025.
The notice of allowance issued on May 14, 2024.

* cited by examiner

*Primary Examiner* — David T Karst
(74) *Attorney, Agent, or Firm* — Harvest IP Law, LLP

(57) ABSTRACT

The present invention relates to a purification method for laurolactam, and more particularly, to a purification method capable of obtaining high-purity laurolactam substantially free of impurities.

The present invention provides a purification method for laurolactam from a reaction product of a laurolactam synthesis process, the production method including: (S1) obtaining a first mixed solid by separating and removing low-boiling point materials through distillation of the reaction product; (S2) removing impurities suspended in a first mixed solution obtained by dissolving the first mixed solid in a good solvent; (S3) obtaining a second mixed solid precipitated by adding a poor solvent to the first mixed solution from which the impurities are removed; and (S4) evaporating a melt obtained by heating and melting the second mixed solid to obtain laurolactam in a gas phase and performing crystallization.

15 Claims, No Drawings

PURIFICATION METHOD FOR LAUROLACTAM

CROSS-REFERENCE TO RELATED APPLICATION(S)

This application is a National Stage of International Application No. PCT/KR2022/001030 filed on Jan. 20, 2022, claiming priority based on Korean Patent Application No. 10-2021-0007868 filed on Jan. 20, 2021, the disclosure of which is incorporated herein by reference in its entirety.

TECHNICAL FIELD

The present invention relates to a purification method for laurolactam, and more particularly, to a purification method capable of obtaining high-purity laurolactam substantially free of impurities.

BACKGROUND ART

In general, in an industrial method for synthesizing a cyclic amide monomer, for example, laurolactam, cyclododecanone oxime is synthesized through Beckmann rearrangement.

Such a polyamide-based polymer material may be synthesized by anionic polymerization, and since the purity of the laurolactam monomer has a great influence on the polymerization reaction activity, the purity of the monomer is a significantly important factor.

Conventionally, laurolactam is purified by removing a solvent by distillation after completion of the reaction of the laurolactam monomer produced by the Beckmann rearrangement, and then removing heavies in a solid phase and/or a liquid phase, but various impurities such as organic matter and ions still remain in a final laurolactam product, resulting in a rapid decrease in activity of the anionic polymerization reaction.

Accordingly, there is a demand for a method for purifying high-purity laurolactam by removing various impurities remaining after the Beckmann rearrangement through a simplified process and increasing anionic polymerization activity of a laurolactam monomer and the like.

As one of these methods, in Korean Patent Laid-Open Publication No. 10-2019-0080535 previously filed by the present applicant, a method for recovering a monomer from which impurities are removed to some extent through distillation and evaporation has been studied.

However, since sticky materials still exist at the interface, anionic reaction sites are damaged during anionic polymerization of a monomer even after recrystallization, and thus, a degree of polymerization may not be increased or a conversion rate decreases.

DISCLOSURE

Technical Problem

An object of the present invention is to provide a purification method capable of obtaining high-purity laurolactam from a product synthesized in a laurolactam synthesis process.

Technical Solution

In one general aspect, a purification method for laurolactam from a reaction product of a laurolactam synthesis process includes: (S1) obtaining a first mixed solid by separating and removing low-boiling point materials through distillation of the reaction product; (S2) removing impurities suspended in a first mixed solution obtained by dissolving the first mixed solid in a good solvent; (S3) obtaining a second mixed solid precipitated by adding a poor solvent to the first mixed solution from which the impurities are removed; and (S4) evaporating a melt obtained by heating and melting the second mixed solid to obtain laurolactam in a gas phase and performing crystallization.

In the purification method for laurolactam according to an embodiment of the present invention, a simple distillation apparatus may be used in the distillation in the step (S1), and during the distillation, a temperature may be 90° C. to 200° C., and a degree of vacuum may be −0.1 to −1 barg.

In the purification method for laurolactam according to an embodiment of the present invention, in the step (S2), the first mixed solid and the good solvent may be mixed at a weight ratio of 1:5 to 10.

In the purification method for laurolactam according to an embodiment of the present invention, a temperature of the good solvent in the step (S2) may be 40° C. to 80° C.

In the purification method for laurolactam according to an embodiment of the present invention, in the step (S3), the good solvent in the step (S2) and the poor solvent may be mixed at a weight ratio of 1:0.5 to 2.

In the purification method for laurolactam according to an embodiment of the present invention, the good solvent and the poor solvent may be miscible.

In the purification method for laurolactam according to an embodiment of the present invention, the step (S3) may be performed using a difference in solubility between the catalyst and laurolactam in the good solvent.

In the purification method for laurolactam according to an embodiment of the present invention, after the step (S3) and before the step (S4), (S3-1) obtaining a second mixed solid precipitated by re-adding a poor solvent to a residue obtained by separating the second mixed solid may be repeated one or more times to repeatedly obtain a second mixed solid.

In the purification method for laurolactam according to an embodiment of the present invention, the step (S3-1) may be repeated one to three times.

In the purification method for laurolactam according to an embodiment of the present invention, a temperature of the poor solvent in the step (S3) may be 50° C. to 100° C.

In the purification method for laurolactam according to an embodiment of the present invention, the heating in the step (S4) may be performed at a degree of vacuum of −0.1 barg to −1 barg.

In the purification method for laurolactam according to an embodiment of the present invention, in the step (S4), laurolactam may be obtained by vaporizing 50% to 70% of the total volume of the melt.

In the purification method for laurolactam according to an embodiment of the present invention, the good solvent may be a C1 to C4 hydrocarbon organic solvent containing one or two or more functional groups selected from the group consisting of a hydroxy group, an amine group, and a thiol group.

In the purification method for laurolactam according to an embodiment of the present invention, the poor solvent may be distilled water or deionized water.

In the purification method for laurolactam according to an embodiment of the present invention, the laurolactam synthesis process may be performed through Beckmann rearrangement of cyclododecanone oxime in the presence of a cyanuric chloride (TCT) catalyst, and the Beckmann rearrangement may be performed to synthesize cyclododecanone oxime into laurolactam by the cyanuric chloride (TCT) catalyst in the presence of a solvent containing isopropylcyclohexane (IPCH).

In another general aspect, there is provided a laurolactam composition purified by the purification method for laurolactam.

In the laurolactam composition according to an embodiment of the present invention, the laurolactam composition may have a purity of laurolactam of 99% or higher.

In still another general aspect, a method for preparing polylaurolactam includes subjecting the laurolactam composition to anionic polymerization in the presence of an anionic initiator to prepare polylaurolactam.

In the method for preparing polylaurolactam according to an embodiment of the present invention, a degree of polymerization of the polymerized polylaurolactam may be 70% or more.

Advantageous Effects

In the purification method for laurolactam according to the present invention, high-purity laurolactam may be obtained.

The laurolactam purified through such a purification method may have a high degree of polymerization.

BEST MODE

Unless otherwise defined, all the technical terms and scientific terms used in the present specification have the same meanings as commonly understood by those skilled in the art to which the present invention pertains. The description for the known function and configuration unnecessarily obscuring the gist of the present invention will be omitted in the following description and the accompanying drawings.

In addition, unless the context clearly indicates otherwise, the singular forms used in the present specification may be intended to include the plural forms.

In addition, units used in the present specification without special mention are based on weight, and as an example, a unit of % or a ratio means wt % or a weight ratio. Unless otherwise defined, wt % means wt % of any one component in a composition with respect to the total weight of the composition.

In addition, a numerical range used in the present specification includes upper and lower limits and all values within these limits, increments logically derived from a form and span of a defined range, all double limited values, and all possible combinations of the upper and lower limits in the numerical range defined in different forms. Unless otherwise specifically defined in the specification of the present invention, values out of the numerical range that may occur due to experimental errors or rounded values also fall within the defined numerical range.

In the present specification, the expression "comprise(s)" is intended to be an open-ended transitional phrase having an equivalent meaning to "include(s)", "contain(s)", "have (has)", and "is (are) characterized by", and does not exclude elements, materials, or steps, all of which are not further recited herein.

In addition, the term "substantially" used in the present specification means that a specific element, material, or step that is not listed in combination with another element, material, or step may be present in an amount having no unacceptably significant influence on at least one basic and novel technical idea of the present invention.

The present invention provides a purification method for laurolactam from a product of a laurolactam synthesis process, and the purification method includes: (S1) obtaining a first mixed solid by separating and removing low-boiling point materials through distillation of the reaction product; (S2) removing impurities suspended in a first mixed solution obtained by dissolving the first mixed solid in a good solvent; (S3) obtaining a second mixed solid precipitated by adding a poor solvent to the first mixed solution from which the impurities are removed; and (S4) evaporating a melt obtained by heating and melting the second mixed solid to obtain laurolactam in a gas phase and performing crystallization.

Conventionally, a method for recovering a monomer from which impurities are removed to some extent through distillation and evaporation of a product has been studied. However, since sticky materials still exist, anionic reaction sites are damaged during anionic polymerization of the monomer even after recrystallization, and thus, a degree of polymerization may not be increased or a conversion rate decreases.

In the purification method of the present invention, high-purity laurolactam may be obtained from a product produced according to the laurolactam synthesis process, and when the high-purity laurolactam obtained by the production method of the present invention is polymerized, a degree of polymerization may be high.

In the present invention, the laurolactam synthesis process may be performed through Beckmann rearrangement of cyclododecanone oxime in the presence of a cyanuric chloride (TCT) catalyst, and the Beckmann rearrangement may be performed to synthesize cyclododecanone oxime into laurolactam by the cyanuric chloride (TCT) catalyst in the presence of a solvent containing isopropylcyclohexane (IPCH), but is not limited thereto.

The Beckmann rearrangement may be performed at a temperature of 70 to 130° C., preferably 90 to 110° C., and more preferably 95 to 100° C. for 1 to 20 minutes, preferably 5 to 20 minutes, and more preferably 5 to 15 minutes. In the reaction, when the reaction temperature is excessively high, a large amount of by-products such as heavies is produced, and when the reaction temperature is too low, a reaction rate is not sufficiently rapid, and it is difficult to apply the Beckmann rearrangement to a commercial process. In addition, when the reaction time is shorter than 1 minute, cyclododecanone oxime may not be sufficiently rearranged into laurolactam, and when the reaction time is longer than 20 minutes, a side reaction occurs excessively, which is not preferable.

Meanwhile, the Beckmann rearrangement refers to rearrangement of keto oxime into an acid amide, and in particular, in the present invention, may refer to a reaction of rearrangement of the cyclododecanone oxime into laurolactam.

The catalyst is cyanuric chloride (TCT). Specifically, the catalyst may be included in an amount of 0.1 to 10 parts by weight, preferably 0.1 to 5 parts by weight, and more preferably 0.5 to 2 parts by weight, with respect to 100 parts by weight of the cyclododecanone oxime. When the content of the catalyst is too low, the Beckmann rearrangement may not be sufficiently performed, and when the content of the catalyst is excessively high, a catalyst material remains at a high content in a reaction product after completion of the reaction, and thus, it is difficult to effectively remove the catalyst material in a purification step.

More specifically, the catalyst may contain cyanuric chloride and zinc chloride at a weight ratio of 2:1 to 1:1, preferably at a weight ratio of 1.5:1 to 1:1, and more preferably at a weight ratio of 1.3:1 to 1:1. Therefore, a decrease in conversion rate according to a moisture content limited by the Beckmann rearrangement may be suppressed to effectively synthesize laurolactam, and the catalyst remaining in the reaction product after completion of the reaction may be easily removed only by a simplified process.

As the solvent, for example, an organic solvent containing isopropylcyclohexane (IPCH) is preferable. The solvent may be used to successfully prepare laurolactam from cyclododecanone oxime using Beckmann rearrangement by a strong non-polarity characteristic.

The organic solvent containing IPCH may be used in an amount of 30 to 50 parts by weight with respect to 100 parts by weight of the cyclododecanone oxime. When the organic solvent containing IPCH is included in the above content range, it is easy to perform the Beckmann rearrangement, and the solvent may be easily removed by distilling the reaction product.

Hereinafter, steps for obtaining high-purity laurolactam by purifying the reaction product obtained through the method described above will be described in detail.

Specifically, first, a step (S1) of obtaining a first mixed solid by separating and removing low-boiling point materials through distillation of the reaction product is performed.

In the present invention, the first mixed solid may refer to a reaction product from which low-boiling point materials are removed by distillation. In this case, the low-boiling point materials may be IPCH and cyclododecanone.

The distillation in the step (S1) may be performed by a distillation apparatus known in the art, and preferably, may be performed by a simple distillation apparatus. When the distillation is performed using a simple distillation apparatus, a temperature and a degree of vacuum may be appropriately adjusted according to a boiling point of the low-boiling point material to be separated, and preferably, the temperature may be 90° C. to 200° C., specifically, 120° C. to 180° C., and more specifically, 140° C. to 160° C., and the degree of vacuum may be −0.1 to −1 barg. In the above ranges, a removal rate of the low-boiling point materials to be removed in this step may be high. Specifically, isopropylcyclohexane (IPCH) used as a solvent may be effectively removed, and at the same time, the removal rate of cyclododecanone (CDON), which is an intermediate product in the Beckmann rearrangement, may be high.

Next, a step (S2) of removing impurities suspended in a first mixed solution obtained by dissolving the first mixed solid in a good solvent is performed.

In the present invention, the impurities may be a particulate catalyst contained in the first mixed solid, but are not limited thereto, and may be suspended by the first mixed solution and may contain a material other than laurolactam.

The good solvent may be a C1 to C4 hydrocarbon organic solvent, preferably a C1 to C4 hydrocarbon organic solvent containing one or two or more functional groups selected from the group consisting of a hydroxy group, an amine group, and a thiol group, and still more preferably a C1 to C4 hydrocarbon containing a hydroxy group or a C1 to C4 alcohol.

When the good solvent is mixed, the catalyst may be removed using a difference in solubility between the catalyst and the good solvent for laurolactam. Specifically, the catalyst is not dissolved in the good solvent and is precipitated as solid particles. On the other hand, laurolactam has a high solubility in the good solvent, and thus, may be all substantially dissolved in the good solvent and may not be precipitated. Thereafter, the catalyst precipitated as particles may be easily removed with a filter. In this case, when the amount of the good solvent injected is too small, a part of laurolactam is not dissolved but exists as a solid and may be removed from the filter together with a residual catalyst, such that a yield of laurolactam decreases, and the part of laurolactam which is not dissolved in the good solvent may be agglomerated with the residual catalyst and may remain after passing through the filter. On the contrary, when the amount of the good solvent injected is too large, it may not be easy to recrystallize laurolactam in a subsequent step (S3). Therefore, the laurolactam synthesized in the step a) and the good solvent may be mixed at a weight ratio of 1:5 to 1:10, preferably at a weight ratio of 1:5 to 1:7, and more preferably at a weight ratio of 1:6 to 1:7.

In this case, it may be advantageous for a dissolution rate of laurolactam when a temperature of the good solvent is 40° C. to 80° C., and specifically, 50 to 60° C.

Meanwhile, in the specification of the present invention, the good solvent may refer to a solvent that has high affinity with laurolactam (solute) and may dissolve laurolactam well, and the poor solvent may refer to a solvent that has low affinity with laurolactam and does not dissolve laurolactam well.

Continuously, the step (S3) is a step of obtaining a second mixed solid precipitated by adding a poor solvent to the first mixed solution from which the impurities are removed in the step (S2). As the poor solvent, a material miscible with the good solvent may be adopted, and specifically, distilled water or deionized water may be used. When the poor solvent is mixed, laurolactam may be precipitated using a difference between the solubility of laurolactam in the good solvent and the solubility of laurolactam in the poor solvent. Specifically, laurolactam has high solubility in the good solvent and low solubility in the poor solvent, and when the poor solvent is mixed with the good solvent in which laurolactam is dissolved in the step (S2), the solubility of laurolactam decreases as a concentration of the good solvent decreases, and as a result, laurolactam may be recrystallized and precipitated as a solid. Thereafter, the precipitated second mixed solid may be obtained by filtration with a filter.

The good solvent and the poor solvent may be injected, for example, at a weight ratio of 1:0.5 to 1:2, and preferably at a weight ratio of 1:0.8 to 1:1.5. When the good solvent is injected in excess as compared with the poor solvent, a part of laurolactam is not precipitated as a solid and may be present in a state of being dissolved in the good solvent, and the yield of purified laurolactam may decrease, which is not preferable.

A temperature of the poor solvent in the step (S3) may be 50° C. to 100° C., and specifically, 60 to 70° C., but is not limited thereto. However, when the poor solvent at a temperature within the above range is used, a concentration of chloride ions remaining in the second mixed solid may be decreased, such that higher-purity laurolactam may be obtained.

In an embodiment of the present invention, after the step (S3) and before the step (S3), the purification method may further include a step (S3-1) of obtaining a second mixed solid precipitated by re-adding a poor solvent to a residue obtained by separating the second mixed solid, and the second mixed solid may be repeatedly obtained from the first mixed solution by repeating this step one or more times. Such a step may further increase the yield of laurolactam by increasing a recovery rate of laurolactam. Specifically, the step (S3-1) is preferably performed fewer than ten times, and specifically, one to three times in terms of process efficiency.

Next, a step (S4) of evaporating a melt obtained by heating and melting the second mixed solid to obtain laurolactam in a gas phase and performing crystallization is performed.

The heating in the step (S4) is not limited as long as it is performed under a condition in which the second mixed solid may be melted, and may be performed at a temperature higher than a melting temperature of laurolactam, specifically, 150° C. to 220° C., and more specifically, 150° C. to 170° C., but is not limited thereto. The heating may be performed at a degree of vacuum of −0.1 to −1. When the heating is performed in a state of reduced pressure within the above range, oxidation by oxygen is prevented in the heating process, such that higher-purity laurolactam may be obtained.

In the step (S4), the evaporation may be performed by an evaporation or distillation apparatus known in the art, and the crystallization may be performed by a crystallization apparatus known in the art.

Specifically, the evaporation may be performed at a temperature of 150° C. to 220° C., and specifically, 160° C. to 220° C., but is not limited thereto, and in this case, the degree of vacuum is not limited as long as it is less than 0.1 bar, and the evaporation may be performed for 30 minutes to 1 hour.

In the step (S4), it is preferable that the second mixed solid is completely melted and then evaporated. When the evaporation is performed in a state where the second mixed solid is not completely melted, it may be difficult to obtain high-purity laurolactam due to a popping phenomenon of heavies included in the melt.

In an embodiment of the present invention, in the step (S4), laurolactam may be obtained by vaporizing only 30% to 90%, and specifically, 50% to 70% of the total volume of the melt. When laurolactam is obtained by vaporizing the entire melt at once and then performing crystallization, laurolactam contaminated by heavies may be obtained due to the popping phenomenon of heavies.

As a specific example, only 50% to 70% of the total volume of the melt may be evaporated and then crystallized to obtain laurolactam, and then only 50% to 70% of the residue may be evaporated again and then crystallized to obtain laurolactam, and this process may be repeatedly performed.

In contrast, in a case of a continuous process, only 50% to 70% of the total volume of the melt may be evaporated and crystallized to obtain laurolactam, and an amount of the melt as much as the vaporized amount may be evaporated and crystallized while being continuously supplied to continuously obtain laurolactam.

The present invention provides a laurolactam composition purified by the purification method described above, and provides a high-purity laurolactam composition containing almost no impurities as it is purified by the purification method described above. Specifically, the laurolactam composition of the present invention has a purity of laurolactam of 99%, and preferably 99.5% or higher, which is significantly high.

In addition, the laurolactam composition may contain a catalyst used in Beckmann rearrangement in an amount of 3 wt % or less, preferably less than 2 wt %, and more preferably 0.1 wt % or less, with respect to the total weight of the laurolactam composition. When the content of the catalyst exceeds the above range, activity of an anionic initiator used in anionic polymerization is significantly killed, such that the polymerization reaction is not easily performed.

In addition, the present invention provides a method for preparing polylaurolactam, the method including subjecting the laurolactam composition to anionic polymerization in the presence of an anionic initiator to prepare polylaurolactam. As the polymerization is performed using the laurolactam composition, polylaurolactam that may have a high degree of polymerization of 70% or more, and more preferably 75% or more may be prepared.

Polymerizaiton of purified laurolactam and an optional new monomer (comonomer) may be performed at 200 to 350° C. for 10 to 60 minutes. Specifically, the polymerization reaction may be performed at 200 to 300° C., and preferably 220 to 250° C. for 10 to 60 minutes, preferably 10 to 50 minutes, and more preferably 20 to 40 minutes.

The polymerized polylaurolactam may be a laurolactam-containing polymer, for example, a copolyamide or a polyether-block amide, and preferably, may be polyamide 12 (nylon 12).

The ionic initiator may include, specifically, one or two or more selected from the group consisting of NaH, LiH, KH, and n-BuLi. A catalyst material used in Beckmann rearrangement according to an embodiment of the present invention is known to significantly kill the activity of the anionic initiator, but in the method for preparing laurolactam according to an embodiment of the present invention and the laurolactam composition obtained by the same, the catalyst material is significantly effectively removed, and thus, a laurolactam monomer may be subjected to anionic polymerization at a high degree of polymerization in the presence of the anionic initiator.

The anionic polymerization may be performed in a batch reactor or a continuous reactor (CSTR, PFR, or PBR), and preferably, may be performed in a continuous reactor, but the present invention is not limited thereto.

Example 1

3 g of cyclododecanone oxime, 12 g of isopropylcyclohexane, and 0.045 g of cyanuric chloride were added to a 100 ml round flask. Then, the temperature was adjusted to 95° C. using a heating mantle, and stirring was performed at 200 rpm or more, thereby preparing a reaction product. A reaction completion time was 5 minutes, a conversion rate of cyclododecanone oxime was 99% or more, and a selectivity of laurolactam was 99% or more.

100 g of the reaction product prepared in the above was injected into a simple distillation apparatus, and distillation was performed at a temperature of 150° C. and a degree of vacuum of −0.9 barg to remove IPCH and CDON through the top of the distillation apparatus.

Thereafter, a content of residual CDON and an LL purity were measured and shown in Table 1. Both the content of residual CDON and the LL purity were measured using gas chromatography. The measuring apparatus used was HP-6890N, and the column used was HP-5 Column.

Then, 700 g of ethanol at 60° C. was injected into a produced brown solid and dissolved in a flask. A suspended solid (catalyst) was removed using a 0.22 μm filter, and 700 g of distilled water at 60° C. was injected into laurolactam (LL) dissolved in ethanol to precipitate an LL solid. The precipitated LL was separated into a solid using a filter. 700 g of distilled water was injected again into laurolactam dissolved in ethanol from which the solid was primarily separated to re-precipitate an LL solid, and this process was repeated a total of three times to precipitate an LL solid.

Thereafter, a concentration of residual chlorine ions was measured and shown in Table 2. The measuring apparatus used was MITSUBISHI AQF-2100H, and the column used was Shodex IC anion column. As an eluent, a mixed solution of 1 mM sodium carbonate ($Na_2CO_3$) and 4 mM sodium bicarbonate ($NaHCO_3$) was used.

Then, the LL solid was injected into a heater having a degree of vacuum of −0.9 barg, and then, the solid was completely melted at 155° C. Thereafter, only 60% of the volume of the melt was vaporized using a film evaporator, heavies were removed through the bottom, and LL was separated through the top. Then, only 60% of the volume of the residual melt was vaporized to remove heavies and separate LL again. A concentration of residual heavies and a yield of inorganic matter (Ash) LL were measured and shown in Table 3. The inorganic matter was measured by TGA thermal analysis. In the recrystallization, there was no sticky or non-separated material between the interfaces.

Subsequently, 50 g of LL and a catalyst were added to a 100 ml round flask at a weight ratio of LL:NaH:ethylene bis stearamide (EBS):tetraethyl orthosilicate (TEOS):CO2=100:0.6:0.36:0.15:0.15 using the prepared LL, an anionic polymerization reaction was performed at 240° C. for 30 minutes to prepare polyamide 12 (PA 12), and a degree of polymerization of PA 12 was shown in Table 4.

Comparative Example 1

100 g of the reaction product prepared in Example 1 was injected into a simple distillation apparatus, and distillation was performed at a temperature of 80° C. and a degree of vacuum of −0.9 barg. A content of residual CDON and an LL purity were measured and shown in Table 1.

Then, the solid was injected into a heater having a degree of vacuum of −0.9 barg, and then, the solid was completely melted at 155° C. Thereafter, 100% of the volume of the melt was vaporized using a film evaporator, heavies were removed through the bottom, and LL was separated through the top. Subsequently, 50 g of LL and a catalyst were added to a 100 ml round flask at a weight ratio of LL:NaH:ethylene bis stearamide (EBS):tetraethyl orthosilicate (TEOS):CO2=100:0.6:0.36:0.15:0.15 using the prepared LL, an anionic polymerization reaction was performed at 240° C. for 30 minutes to prepare polyamide 12 (PA 12), and a degree of polymerization of PA 12 was shown in Table 4.

Comparative Example 2

700 g of ethanol at 60° C. was injected into the brown solid prepared in Example 1 and dissolved in a flask. A suspended solid (catalyst) was removed using a 0.22 μm filter. Thereafter, a concentration of residual chlorine ions was measured and shown in Table 2.

Then, the solid was injected into a heater having a degree of vacuum of −0.9 barg, and then, the solid was completely melted at 155° C. Thereafter, 100% of the volume of the melt was vaporized using a film evaporator, heavies were removed through the bottom, and LL was separated through the top. Subsequently, 50 g of LL and a catalyst were added to a 100 ml round flask at a weight ratio of LL:NaH:ethylene bis stearamide (EBS):tetraethyl orthosilicate (TEOS):CO2=100:0.6:0.36:0.15:0.15 using the prepared LL, an anionic polymerization reaction was performed at 240° C. for 30 minutes to prepare polyamide 12 (PA 12), and a degree of polymerization of PA 12 was shown in Table 4.

Comparative Example 3

The melt prepared in Example 1 was completely vaporized to separate LL. Subsequently, 50 g of LL and a catalyst were added to a 100 ml round flask at a weight ratio of LL:NaH:ethylene bis stearamide (EBS):tetraethyl orthosilicate (TEOS):CO2=100:0.6:0.36:0.15:0.15 using the prepared LL, an anionic polymerization reaction was performed at 240° C. for 30 minutes to prepare polyamide 12 (PA 12), and a degree of polymerization of PA 12 was shown in Table 4.

Comparative Example 4

700 g of ethanol at 60° C. was injected into the brown solid prepared in Example 1 and dissolved in a flask. A suspended solid (catalyst) was removed using a 0.22 μm filter.

Then, the LL solid was injected into a heater having a degree of vacuum of −0.9 barg, and then, the solid was completely melted at 155° C. Thereafter, only 60% of the volume of the melt was vaporized using a film evaporator, heavies were removed through the bottom, and LL was separated through the top. Then, only 60% of the volume of the residual melt was vaporized to remove heavies and separate LL again.

Subsequently, 50 g of LL and a catalyst were added to a 100 ml round flask at a weight ratio of LL:NaH:ethylene bis stearamide (EBS):tetraethyl orthosilicate (TEOS):CO2=100:0.6:0.36:0.15:0.15 using the prepared LL, an anionic polymerization reaction was performed at 240° C. for 30 minutes to prepare polyamide 12 (PA 12), and a degree of polymerization of PA 12 was shown in Table 4.

TABLE 1

| | Comparative Example 1 | Example 1 |
|---|---|---|
| CDON | 0.56% | 0% |
| LL purity | 99.04% | 99.59% |

TABLE 2

| Classification | EtOH washing | Hot water washing | Chlorine ion concentration (ppm) |
|---|---|---|---|
| Comparative Example 1 | X | X | 530 |
| Comparative Example 2 | ○ | X | 130 |
| Example 1 | ○ | ○ | 53 |

TABLE 3

| Classification | Concentration of heavies | Content of inorganic matter (Ash) |
|---|---|---|
| Comparative Example 3 | 0.41% | 1.506% |
| Example 1 | 0 | 0 |

TABLE 4

| | First step | Second step | Third step | Degree of polymerization (g/mol) |
|---|---|---|---|---|
| Example 1 | Simple distillation at 150° C. | EtOH & Hot water | Sequential Partial | 87,793 |
| Comparative Example 1 | Simple distillation at 90° C. | No | Single step | 24,890 |
| Comparative Example 2 | Simple distillation at 150° C. | EtOH | Single step | 36,821 |
| Comparative Example 3 | Simple distillation at 150° C. | EtOH & Hot water | Single step | 79,952 |
| Comparative Example 4 | Simple distillation at 150° C. | EtOH | Sequential Partial | 77,711 |

Referring to Table 1, it could be confirmed that, in the present invention, when the distillation was performed by a simple distillation apparatus, CDON was removed, and thus, high-purity laurolactam was removed.

In addition, referring to Table 2, it could be confirmed that a large amount of chlorine ions was removed by addition of ethanol and distilled water.

Furthermore, through Table 3, it could be appreciated that the removal rate of heavies and inorganic matter was higher when the melt was vaporized to a predetermined volume several times than when the melt was completely vaporized in a single process.

Furthermore, through Table 4, it could be confirmed that, when the laurolactam purified by the purification method of the present invention was polymerized, polyamide having excellent physical properties was obtained at a high degree of polymerization.

Hereinabove, although the present invention has been described by specific matters, limited embodiments, and drawings, they have been provided only for assisting in the entire understanding of the present invention. Therefore, the present invention is not limited to the embodiments. Various modifications and changes may be made by those skilled in the art to which the present invention pertains from this description.

Therefore, the spirit of the present invention should not be limited to the described embodiments, but the claims and all modifications equal or equivalent to the claims are intended to fall within the spirit of the present invention.

The invention claimed is:

1. A purification method for laurolactam from a reaction product of a laurolactam synthesis process, the purification method comprising:

(S1) obtaining a first mixed solid by separating and removing low-boiling point materials through distillation of the reaction product;

(S2) removing impurities suspended in a first mixed solution obtained by dissolving the first mixed solid in a good solvent;

(S3) obtaining a second mixed solid precipitated by adding a poor solvent to the first mixed solution from which the impurities are removed; and (S4) evaporating a melt obtained by heating and melting the second mixed solid to obtain laurolactam in a gas phase and performing crystallization.

2. The purification method of claim 1, wherein a simple distillation apparatus is used in the distillation in the step (S1), and during the distillation, a temperature is 90° C. to 200° C., and a degree of vacuum is −0.1 to −1 barg.

3. The purification method of claim 1, wherein in the step (S2), the first mixed solid and the good solvent are mixed at a weight ratio of 1:5 to 10.

4. The purification method of claim 1, wherein a temperature of the good solvent in the step (S2) is 40° C. to 80° C.

5. The purification method of claim 1, wherein in the step (S3), the good solvent in the step (S2) and the poor solvent are mixed at a weight ratio of 1:0.5 to 2.

6. The purification method of claim 1, wherein the good solvent and the poor solvent are miscible.

7. The purification method of claim 1, wherein the step (S3) is performed using a difference in solubility between the catalyst and the good solvent for laurolactam.

8. The purification method of claim 1, wherein after the step (S3) and before the step (S4), (S3-1) obtaining a second mixed solid precipitated by re-adding a poor solvent to a residue obtained by separating the second mixed solid is repeated one or more times to repeatedly obtain a second mixed solid.

9. The purification method of claim 8, wherein the step (S3-1) is repeated one to three times.

10. The purification method of claim 1, wherein a temperature of the poor solvent in the step (S3) is 50° C. to 100° C.

11. The purification method of claim 1, wherein the heating in the step (S4) is performed at a degree of vacuum of −0.1 barg to −1 barg.

12. The purification method of claim 1, wherein in the step (S4), laurolactam is obtained by vaporizing 50% to 70% of the total volume of the melt.

13. The purification method of claim 1, wherein the good solvent is a C1 to C4 hydrocarbon organic solvent containing one or two or more functional groups selected from the group consisting of a hydroxy group, an amine group, and a thiol group.

14. The purification method of claim 1, wherein the poor solvent is distilled water or deionized water.

15. The purification method of claim 1, wherein the laurolactam synthesis process is performed through Beckmann rearrangement of cyclododecanone oxime in the presence of a cyanuric chloride (TCT) catalyst, and the Beckmann rearrangement is performed to synthesize cyclododecanone oxime into laurolactam by the cyanuric chloride (TCT) catalyst in the presence of a solvent containing isopropylcyclohexane (IPCH).

* * * * *